United States Patent [19]
Doak

[11] Patent Number: 6,064,056
[45] Date of Patent: May 16, 2000

[54] AIR CURTAIN FORMER FOR CREATING AN AIR CURTAIN TO COMPENSATE FOR IMPURITY BUILDUP

[75] Inventor: Arthur G. Doak, Nashville, Tenn.

[73] Assignee: Magnetic Separation System, Inc., Nashville, Tenn.

[21] Appl. No.: 09/060,901

[22] Filed: Apr. 15, 1998

[51] Int. Cl.$^7$ .................................................. G01N 9/04
[52] U.S. Cl. .............................. 250/223 R; 250/223 B; 250/222.1
[58] Field of Search .......................... 250/222.1, 223 R, 250/223 B

[56] References Cited

U.S. PATENT DOCUMENTS

| | | | |
|---|---|---|---|
| 3,809,913 | 5/1974 | Prellwitz | 250/575 |
| 5,192,973 | 3/1993 | Hickisch | 399/93 |
| 5,683,000 | 11/1997 | Low | 209/585 |

*Primary Examiner*—Edward P. Westin
*Assistant Examiner*—Glenn T Kinnear
*Attorney, Agent, or Firm*—Waddey & Patterson, P.C.; Edward D. Lanquist, Jr.

[57] ABSTRACT

This invention presents a method of clearing a sensor field of debris, including liquids, through the use of an air curtain. An embodiment of this invention addresses the problem of impurity buildup in the sensing field of an optical sorter. An air curtain is created which prevents film buildup between the light sensor and the light source by blowing material and impurities, which form the film as they fall off articles being sorted, out of the sensing field.

16 Claims, 3 Drawing Sheets

AIR CURTAIN FORMER FOR CREATING AN AIR CURTAIN TO COMPENSATE FOR IMPURITY BUILDUP

Be it known that I, Arthur G. Doak, a citizen of United States, residing at Nashville, Tenn.; have invented "An Air Curtain Former for Creating an Air Curtain to Compensate for Impurity Buildup."

BACKGROUND OF THE INVENTION

This invention relates to clearing sensors of debris to provide more accurate sensing data. A particular embodiment specifically relates to reducing film buildup over optical sensors in an optical sorting machine due to impurities carried along with the articles to be sorted.

Optical sorting machines, of the type to which an embodiment of this invention relates, work on the principle of light attenuation. Generally, sorters of this type are used to sort articles, such as glass cullet or other material, for post consumer recycling and processing. The glass cullet are intermixed with dirt, sand, and other impurities; it is not economically viable to preclean the cullet. Although optical sorting of glass is offered as an example, the problems of impurity build-up applies to any sorting machine. For example, metallic build-up on an eddy current sensor can affect its operation. Liquid or particulate build-up on a plastic sorting machine can affect its operation.

Optical sorters of this type generally work as follows. The cullet pass through a sensing field where light of different wavelengths is emitted by light sources and sensed by sensors. The sensors generate signals corresponding to the magnitude of light sensed. Cullet of different color attenuate different wavelengths of light different amounts. This attenuated light signal is compared against a baseline value for the signal to determine the color of the cullet.

Impurities carried along with the cullet buildup over the sensors. This shifts the attenuation value and leads to missorts. These missorts may lead to less pure sorted lots. Lower quality lots are, thus, passed on for subsequent processing. Alternatively, cullet having potential value are erroneously discarded due to shifted attenuation readings.

Prior art has attempted to compensate for impurity, or film, buildup by increasing, or lowering, the baseline value over time. This has proved less than satisfactory. One reason for the short fall is that the impurity layer is not uniform. As the film layer builds, cutlet tend to create furrows in the film layer. This results in nonuniformities in the film layer, and tends to lead to missorts.

The prior art has also attempted to solve the problem by cleaning the screen. However, the cleanser can affect the sort.

The prior art has also attempted to solve the problem by repeatedly replacing the wearcover; this increases expense and down time.

What is needed is a device to reduce light attenuation shifts due to film build up in an optical sorting device. This needed system must be efficient and economical. This needed system must decrease down time. This needed system must efficiently clean the sensor area to reduce the effects of particulate and fluid build-up. This needed system is lacking in the prior art.

SUMMARY OF THE INVENTION

This invention presents apparatus and methods to clear sensors of debris through use of an air curtain. Reliability of the sensor data is, thus, improved. Generally, most sensors susceptible to distortion by debris, or impurities, including liquids, in the sensing field, may benefit from this invention. One embodiment of this invention, in particular, addresses the problem of impurity buildup in the sensing field of any sorter including an optical sorter. Buildup of film and other impurities affect the attenuation values because light is attenuated by the film as well as the article to be sorted. These articles are generally glass cullet. Glass cullet, generally, are broken pieces of glass bottles and the like. The shifted attenuation readings lead to article missorts. This invention overcomes attenuation problems due to nonuniformities associated with cullet furrowing.

The nonuniformities in the film layer are overcome by providing a layer of air between the sensors (or sensor) and the cullet. Impurities often fall off often the cutlet as the cullet pass through the sensing field. An air curtain is created which protects the sensors from film buildup by blowing impurities out of the sensing field.

The device which creates the air curtain has an airflow plane below a slide on which cutlet slide. The slide in a cullet sorting machine is frequently called a 'wearcover'. The slide portion of the device ends at the sensing field. In the sensing field emitted light is sensed by sensors and attenuated by cullet.

Between the slide and airflow plane is an air passage. Air is forced through the passage with sufficient force to provide an air curtain. The air curtain blows impurities which fall toward the sensors out of the sensing field, typically downstream, thus, providing an air curtain over the sensors.

Beyond the sensing field, the airflow plane is curved away from the wearcover. The air layer will follow the curved plane. This phenomena of the air layer adhering to the airflow plane is generally referred to as "pneumatic wall attachment." This phenomena is employed to divert the air stream below the path of the cullet. Diverting the air stream below the cutlet path limits the chance that the air curtain may interfere with the ejector. The ejector used with the sorter is generally an air jet, or air valve. After through the sensor field, cullet are then ejected from the cullet stream by an ejector, or allowed to pass.

In one embodiment, the sensors are covered with a transparent cover which is in plane with the airflow plane and below the layer of air. To reduce optical distortion, the transparent cover is adapted to be bonded to the sensors with transparent silicone grease, or similar substance. The silicone grease provides an optical connection medium with properties similar to the transparent cover.

An object of the invention is to provide a device to reduce light attenuation shifts due to film build up in an optical sorting device.

Another object of the present invention is to provide a system for cleaning the sensor area of any sensing system.

Another object of the present invention is to provide a system which is economical to manufacture and use; and may be adapted to use with existing sensing systems.

DESCRIPTION OF THE PREFERRED EMBODIMENTS

Applicant's invention will be best understood when considered in light of the following description of the preferred embodiment of the invention as illustrated in the attached drawings wherein like referenced numerals and characters refer to like parts.

Figure 1:
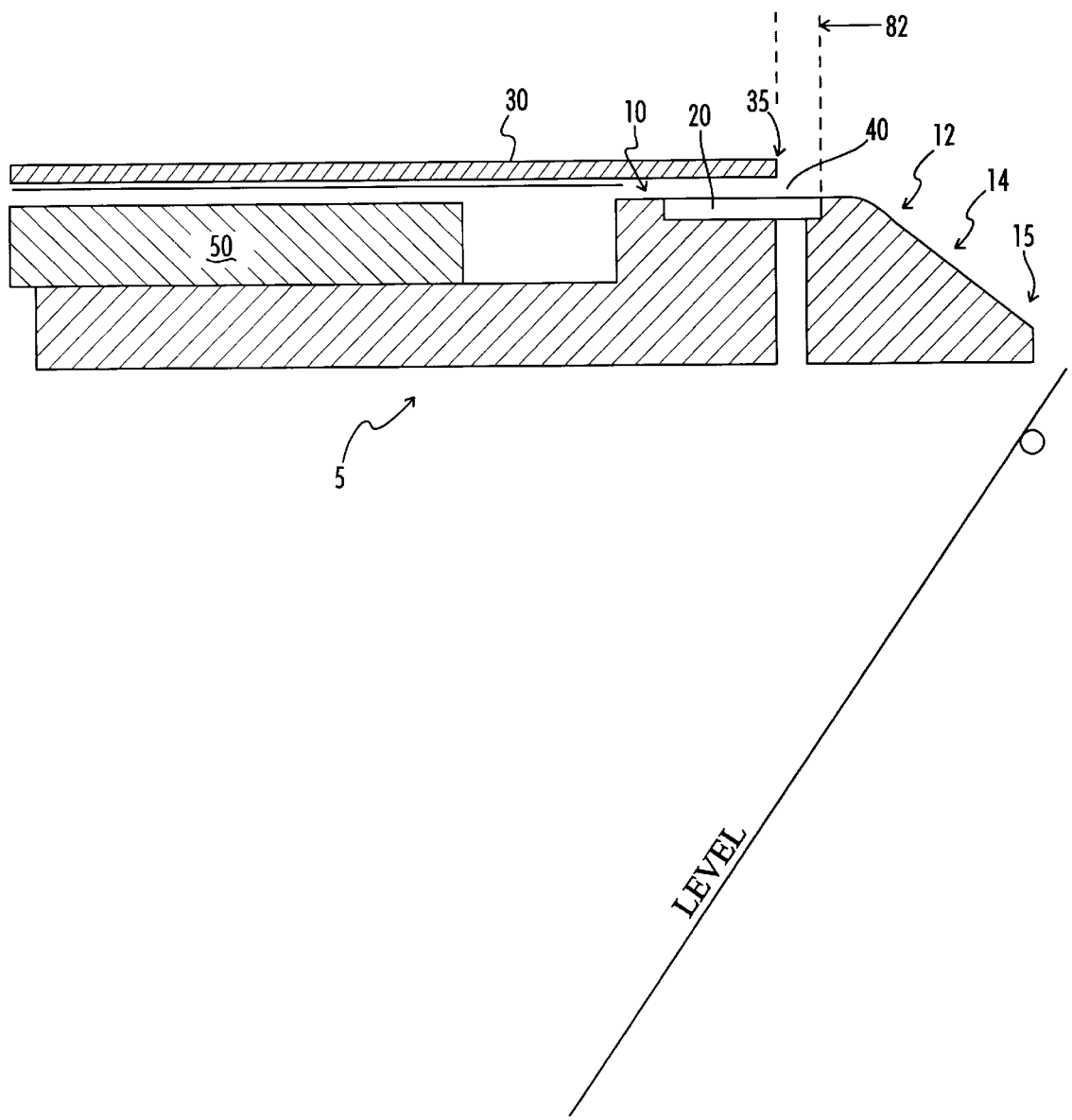
FIG. 1 is a cutaway side view of an air curtain former.

FIG. 1 shows an air curtain former 5. It includes an airflow plane 10 and a transparent cover 20. The transparent cover 20 sits in plane with the airflow plane 10 and below the path an air layer will flow. Beyond the sensing field 82, the airflow plane 10 includes a curve 12 and a terminus 15.

The curve 12 curves away from the path of the cullet to limit possible interference with the ejector jets by the air curtain. The curve 12 and the terminus 15 may be separated by a fall away (14), as in FIG. 1, or merged into a single curve, as in FIG. 3. The curve 12, if used, should be sufficiently gradual so as to maintain a pneumatic wall attachment phenomena.

Figure 2:
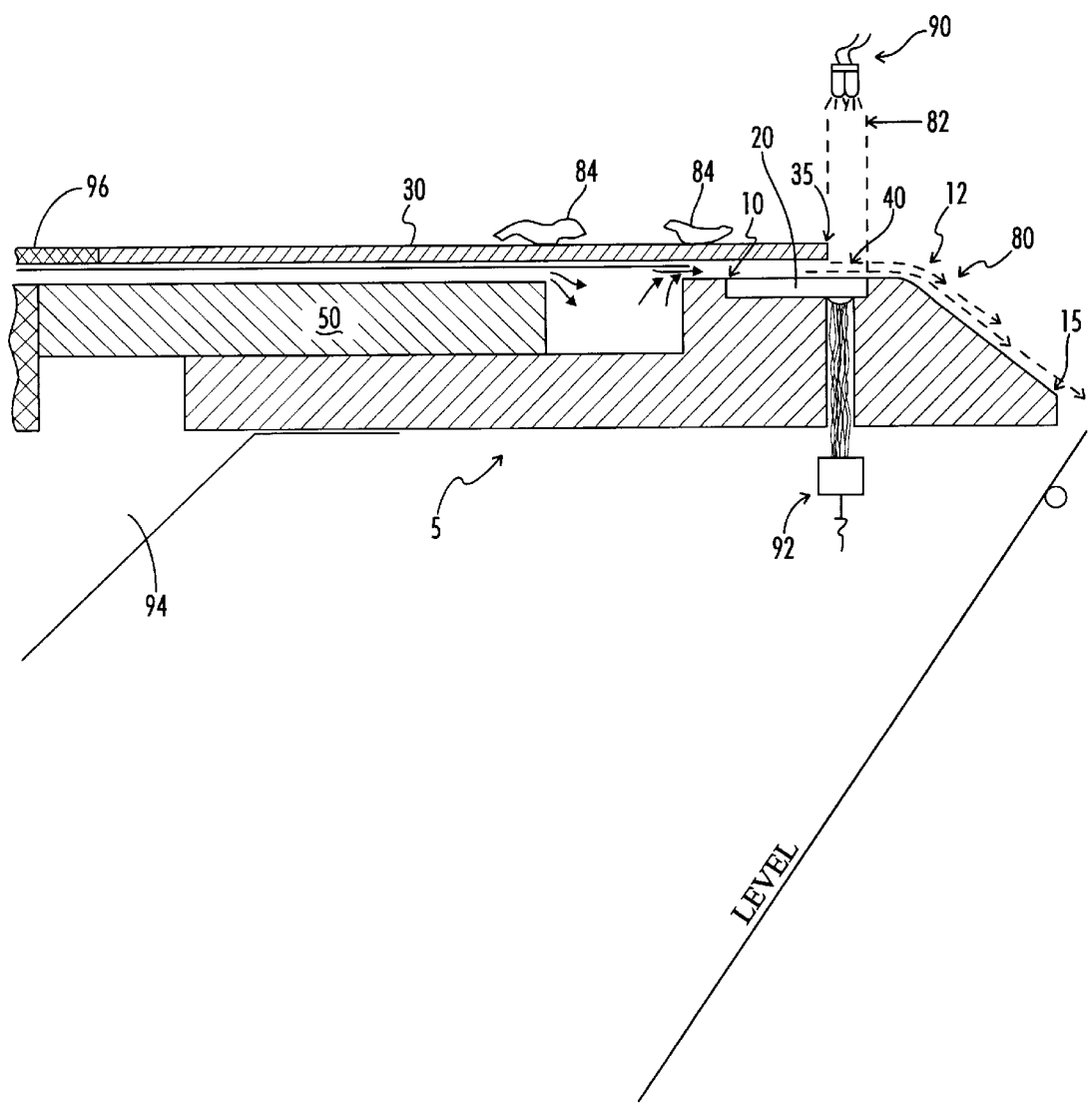
FIG. 2 is a cutaway side view of an air curtain former in connection with an air supply and a sensor.

FIG. 1 also includes a slide (or wearcover) 30 parallel to the airflow plane 10. Together the wearcover 30 and the airflow plane 10 form an air passage 40. The slide 30 includes a terminating end 35 which terminates at the onset of the sensing field 82. FIG. 2 show the slide terminating end 35 ending prior to a plane in which the light source 90 and the light sensor lie 92.

In one embodiment, the airflow plane curve 12 is downstream of the plane in which the light 90 and the sensor 92 lie. Downstream is defined in the direction of the cullet path. A fluid conduit 50 for conducting air supplied to the air passage is also shown in FIG. 1.

FIG. 2 shows an air curtain former 5 substantially similar to the air curtain former shown in FIG. 1, however, it is shown with the light source 90 the light sensor 92, and the cullet 84. The forced air layer 80 which flows through the air passage 40 is also shown in FIG. 2. The air layer 80, as shown, adheres to the airflow plane 10 around the curve 12 of the airflow plane 10. An upstream slide 96 delivers cullet 84 to the air curtain former 5; the cullet then pass through the sensing field 82.

Figure 3:
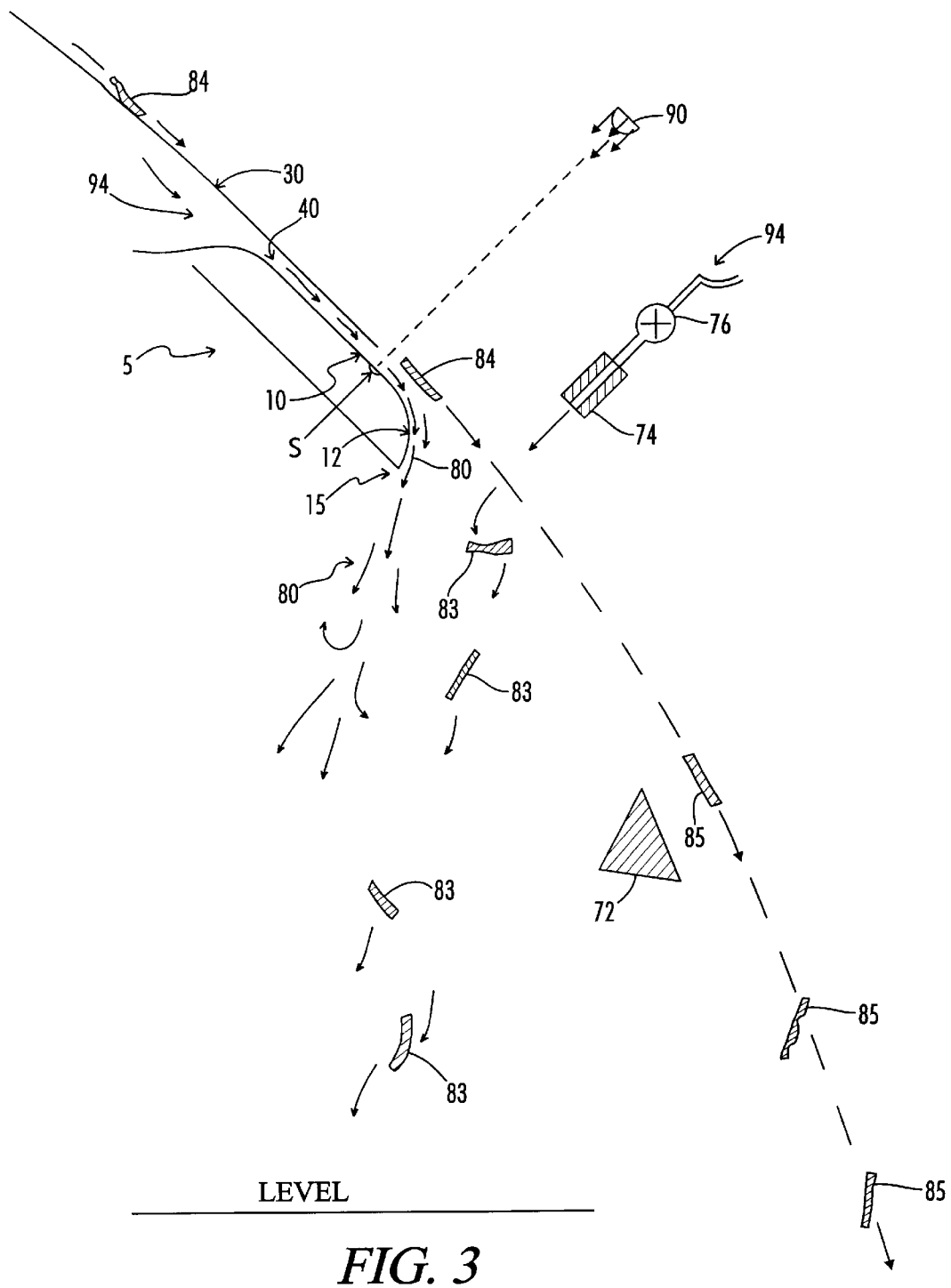
FIG. 3 is a cutaway side view of an air curtain former in operation with an ejector.

FIG. 3 shows an air curtain former 5 substantially similar to the air curtain former shown in FIGS. 1 and 2. FIG. 3 further shows an ejector system 70 including a splitter 72, an ejector nozzle 74 and a solenoid valve 76. The solenoid valve 76 allows air from an air supply 94 to eject ejected material 83 and allow non-ejected material 85 to pass downstream.

The preferred embodiment is an air curtain former 5 for forming an air curtain to compensate for false signal readings which are due to dirt, film, and other impurities building up between the light sensor 92 and the light source 90. The light sensor 92 senses the emitted light and generates signals. The signals have amplitudes corresponding to the magnitude of the light sensed.

It will be apparent to those skilled in the art of sensors, that the invention may be used to clear foreign material, including debris, film, liquid, and the like, from a multitude of sensor types. Some sensor types that may benefit from an air curtain to clear the sensing field include those that use magnetic fields, electromagnetic fields (including thermal and nuclear radiation), acoustic fields, and optical sensing. Generally, any sensor field which may be distorted by impurities, and not effected by air flow, may benefit from the invention. In those systems which may be interfered with by air flow, the air curtain may be adapted to limit, or avoid, interference by the air flow. The curve 12 shown in FIGS. 1 through 3 is an example of one such adaptation; it diverts air away from the cullet stream using pneumatic wall phenomena.

Referring to an optical sorting machine of the type in which a preferred embodiment of this invention is used, when cullet 84 pass through the sensing field 82, the cullet 84 attenuate the light sensed. Different color cullet 84 attenuate different wavelengths of light different amounts. For instance a red cullet would attenuate a green light wavelength more than a red light wavelength. The attenuated signal is compared to a baseline amplitude value for the given wavelength of light; color of the cullet can be determined from an attenuation analysis.

Cullet are, however, intermixed with film, dirt, sand and the like. Cullet carry this film with them through the sensing field 82. The film rubs off and is deposited on the sensor 92. The film layer further attenuates the light source 90; this leads to false optical signal readings. Missorted cullet 84 result from this attenuation shift.

An airflow plane 10 is oriented parallel to the path of the cullet 84. The airflow plane 10 is adapted to receive the light sensor 92. A transparent cover 20 fits in plane with the airflow plane 10 and beneath the path an air layer 80 will take. The transparent cover 20 covers and protects the sensor 92. The transparent cover 20 is adapted to be bonded to the sensor 92 with transparent silicone grease. The silicone grease should be packed in and around the sensor 92 and up against the transparent cover 20. This reduces bending and light defraction as the emitted light passes through different mediums. The silicone grease has properties more similar to the transparent cover than air, so the light rays are bent less than if they were to pass through an air medium after passing through the transparent cover 20 before being sensed by the sensors 92.

One of the preferred embodiments also includes a slide (or wearcover) 30 which is oriented parallel to the airflow plane 20. The wearcover 30 is offset from the airflow plane 10 to form an airflow passage 40. The wearcover 30 has a terminating end 35 which abuts the sensing field 82. The other end of the wearcover 30 mates with an upstream slide 96. The upstream slide 96 provides a means for the cullet 84 to ultimately reach the sensing field 82.

A fluid conduit 50 conducts air supplied from an air supply 94 to the airflow passage 40 such that an air layer 80 flows along the airflow plane 10. Film and impurities are thereby blown off of, and away from, the sensor 92 as the cullet pass through the sensing field 82.

The airflow plane 10 has a terminus 15 and a curve 12. The curve 12 is curved away from the cutlet path. It is sufficiently curved to divert the air layer 80 away from the cullet path. If the curve 12 is curved or bent too sharply, the air layer 80 will not adhere to the wall. If the air layer 80 is not diverted, it may interfere with passage of material through the ejector.

Cullet are then ejected from the cullet stream by the ejector system 70, or allowed to pass. One such ejector system 70 employs a splitter 72 and air forced through an ejector nozzle 74. The ejector nozzle 74 is attached to an air supply. A solenoid valve 76 operates to allow air through the ejector nozzle 74 and blow ejected material 83 out of the path of non-ejected material 85. The non-ejected material, or accepted cullet, continue downstream.

Because there is no film buildup to attenuate the light, the light is only attenuated by the passing cullet, and the attenuated light more accurately represents the colors of the cullet. The more accurate color distinction results in fewer missorts which improves purity of the sorted lot and increases the material to be processed on down the line. Because the sensor was cleared of attenuating debris in an economical manner, greater profit is derived from the purer sorted lot.

Thus, although there have been described particular embodiments of the present invention of "Air Curtain Former for Creating an Air Current to Compensate for Impurities," it is not intended that such references be construed as limitations upon the scope of this invention except as set forth in the following claims.

What is claimed is:

1. A device to form an air curtain to prevent a film buildup in a sensing field, said device comprising:
    an airflow plane aligned with a path of articles and offset a distance from said path;
    a slide over which articles slide, said slide disposed between the article path and said airflow plane, wherein said slide is offset from said airflow plane such that said slide and said airflow plane define an air passage; and
    a fluid conduit adapted to conduct air from an air supply to said air passage such that film is prevented from building up in the sensing field, said fluid conduit in fluid conductivity with said air passage.

2. A device to compensate for false optical signal readings due to dirt, film, and other impurities building up between a light sensor and a light source, where the light sensor is capable of sensing light and generating signals having amplitudes corresponding to magnitudes of a light sensed by the light sensor, and the light source is capable of emitting light, and where the light sensor and the light source are positioned such that a cullet path passes through the emitted light and attenuates the light sensed by the light sensor, thus allowing for sorting of cullet based upon an amount the sensed light is attenuated compared to a baseline amplitude value, said device comprising:
    an airflow plane parallel to the cullet path and offset a distance from the cullet path, where said airflow plane is adapted to receive the light sensor;
    a wearcover over which cullet slide disposed between the cullet path and said airflow plane, the wearcover offset a spaced distance from said airflow plane so that said wearcover and said airflow plane form an airflow passage in said spaced distance there between, where said airflow passage is adapted to receive air and direct air between the light sensor and the cullet path; and
    a fluid conduit adapted to conduct air from an air supply to said air passage, said fluid conduit adapted to be in fluid conductivity with said airflow passage such that air may be conducted from the air supply to said airflow passage.

3. The device of claim 2, wherein the wearcover includes a terminating end, said terminating end terminating prior to a plane in which the light sensor and the light source lie.

4. The device of claim 3, wherein said airflow plane includes a terminus, said terminus located downstream of the plane in which the light sensor and the light source lie, wherein downstream is defined by a cullet path direction.

5. The device of claim 4, wherein said airflow plane terminus is curved away from the cullet path, and said curve is sufficiently gradual so as to maintain a pneumatic wall attachment phenomena.

6. The device of claim 2, wherein said airflow plane is further adapted to receive a transparent cover adapted to be received in said airflow plane to cover the light sensor.

7. The device of claim 6, wherein said transparent cover is further adapted to be in optical connection with the light sensor.

8. The device of claim 7, wherein said optical connection includes silicone grease.

9. The device of claim 7 wherein the wearcover includes a terminating end, said terminating end terminating prior to a plane in which the light sensor and the light source lie.

10. The device of claim 9, wherein said airflow plane includes a terminus, said terminus being located downstream of the plane in which the light sensor and the light source lie, wherein downstream is defined by the cullet path direction.

11. The device of claim 10, wherein said airflow plane terminus is curved away from the cullet path, and said curve is sufficiently gradual so as to maintain a pneumatic wall attachment phenomena.

12. An air curtain former to compensate for false optical signal readings due to film building up between a light sensor and a light source in an optical sorting machine, wherein the light source emits light, the light sensor senses the emitted light and generates signals corresponding to the magnitude of sensed light sensed by the sensor, and the light sensor and the light source are positioned such that a cullet path passes through the sensed light, thereby attenuating the sensed light, thus allowing for optical sorting of cullet based upon an amount the sensed light is attenuated compared to a baseline amplitude value, said air curtain former comprising:
    an airflow plane parallel to the cullet path and offset a distance from the path of cullet, said airflow plane adapted to receive the light sensor;
    a wearcover over which cullet slide disposed between the cullet path and said airflow plane and offset a spaced distance from said airflow plane, where said wearcover and said airflow plane define an airflow passage there between, and where said airflow passage is adapted to direct air between the light sensor and the cullet path so that film does not buildup between the light sensor and the light source; and
    a fluid conduit in fluid connectivity with said airflow passage such that air may be conducted from an air supply to said airflow passage.

13. The air curtain former of claim 12, wherein said airflow plane is further adapted to receive a transparent cover adapted to be received in said airflow plane to cover the light sensor such that air may be directed between said transparent cover and the cullet path, and where said transparent cover is further adapted to be in optical connection with the light sensor.

14. The air curtain former of claim 13, wherein said airflow plane includes a terminus, said terminus located downstream of the sensed light, wherein downstream is defined by the cullet path direction.

15. The air curtain former of claim 14, wherein said terminus of said airflow plane is curved away from the cullet path, where said curve is sufficiently gradual so as to maintain a pneumatic wall attachment phenomena.

16. A method to limit false optical signal readings due to film buildup between a light sensor and a light source in an optical sorting machine, wherein the light source emits light and the light sensor senses the emitted light, generates signals corresponding to the magnitude of sensed light sensed by the sensor, and where the light sensor and the light source are positioned such that cullet pass through the sensed light, thereby attenuating the sensed light, thus allowing for optical sorting of cullet based upon an amount the sensed light is attenuated compared to a baseline amplitude value, said method comprising the step of propagating air between the light sensor and a cullet path; and placing an airflow plane an offset distance from a wearcover such that the wearcover is between the cullet path and the airflow plane and the wearcover and the airflow plane form the air passage.

* * * * *